(12) United States Patent
Suzuki

(10) Patent No.: US 8,382,783 B2
(45) Date of Patent: Feb. 26, 2013

(54) MEDICAL HANDPIECE

(75) Inventor: Tetsuji Suzuki, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 0 days.

(21) Appl. No.: 12/509,804

(22) Filed: Jul. 27, 2009

(65) Prior Publication Data

US 2009/0287234 A1    Nov. 19, 2009

Related U.S. Application Data

(63) Continuation of application No. 11/746,409, filed on May 9, 2007, now abandoned.

(30) Foreign Application Priority Data

May 11, 2006    (JP) .................................. 2006-132595

(51) Int. Cl.
    *A61B 17/32*    (2006.01)

(52) U.S. Cl. .......................... 606/170; 606/171; 606/180

(58) Field of Classification Search .................. 606/180, 606/167, 170, 171
    See application file for complete search history.

(56) References Cited

U.S. PATENT DOCUMENTS

2006/0041268 A1    2/2006    Shores et al.

FOREIGN PATENT DOCUMENTS

| EP | 1598023 A2 * | 11/2005 |
| JP | 2004-097790 A | 4/2004 |
| JP | 2005-328971 A | 12/2005 |

* cited by examiner

*Primary Examiner* — Gary Jackson
*Assistant Examiner* — Kevin Everage
(74) *Attorney, Agent, or Firm* — Jason D. Voight

(57) ABSTRACT

The medical handpiece of the present invention includes a cutting tool having a flexible shank and a cutting bur, a plastically deformable tubular casing for the cutting tool, a handpiece body detachably holding the cutting tool, bearing members disposed in the casing, an inner intervening member for receiving the shank, and an outer intervening member arranged around the inner intervening member. The inner and outer intervening members are composed of a plurality of segments, and each segment is arranged between or on distal or proximal side of the bearing members. Each segment of the outer intervening member is further composed of a plurality of sub-segments. Annular members having the outer diameter that is larger than that of the outer intervening member are arranged between the sub-segments of the outer intervening member. The present handpiece provides improved operationality since shaking is hardly generated even when the casing is flexed.

5 Claims, 4 Drawing Sheets

MEDICAL HANDPIECE

This is a continuation of application Ser. No. 11/746,409, filed May 9, 2007, now abandoned, and claims priority to Japanese application no. 2006-132595, filed May 11, 2006.

FIELD OF ART

The present invention relates to a medical handpiece for cutting a treatment site with a cutting tool that is rotatably driven by power transmitted from a drive source.

BACKGROUND ART

Medical handpieces having a cutting tool that is rotatably driven by power from a drive source, such as a motor, to cut a treatment site, is disclosed, for example, in JP-2004-97790-A.

The medical handpiece disclosed in this publication has a cutting tool which has a bur provided at the tip of a flexible shank, and is inserted and placed in a tubular casing. The cutting tool is detachably held in a handpiece body, and rotatably driven by power transmitted from a drive source. Between the casing and the shank is disposed a tubular intervening member. This medical handpiece is designed such that the casing, the intervening member, and the cutting tool may be flexed for a predetermined angular range, where the intervening member prevents the shank from contacting the inner surface of the casing in the curved portion.

Further, there is disclosed in JP-2005-328971-A a medical handpiece wherein inner and outer intervening members are arranged one in another between a plurality of bearings for inhibiting shaking and deterioration of durability by friction heat, which are caused by contact between the shank and the intervening members.

In the prior art medical handpiece discussed above, the deterioration of durability by friction heat generated by the contact between the shank and the inner intervening member could be inhibited. However, when the casing is flexed for a relatively large angle from its axis, the inner intervening member is pressed by the outer intervening member to be brought into contact with the shank, which is loaded accordingly. It is found that this causes new problems to be solved, i.e., rattling, increased shaking during rotation, and deterioration of operationality of the medical handpiece.

SUMMARY OF THE INVENTION

The present invention aims to solve such problems in the prior art. It is an object of the present invention to provide a medical handpiece with improved operationality wherein shaking is hardly generated even when the casing is flexed.

According to the present invention, there is provided a medical handpiece comprising:

a cutting tool having a flexible shank and a cutting bur provided at a distal end of said shank for cutting a treatment site, a tubular casing for receiving the cutting tool therein, wherein said casing and said cutting tool are flexible for a predetermined angular range, where the casing undergoes plastic deformation and the shank of the cutting tool undergoes elastic deformation, a handpiece body detachably holding a proximal end of the cutting tool and transmitting power from a drive source to the cutting tool, a plurality of bearing members disposed in the casing, an inner flexible tubular intervening member for receiving the shank of the cutting tool therein, wherein said inner intervening member is composed of a plurality of segments, each segment being arranged between or on distal or proximal side of said bearing members, and an outer flexible tubular intervening member arranged around said inner intervening member, wherein said outer intervening member is composed of a plurality of segments, each segment being arranged between or on distal or proximal side of said bearing members, wherein each segment of said outer intervening member is further composed of a plurality of sub-segments, and a plurality of annular members having the outer diameter larger than the outer diameter of said outer intervening member are arranged between said sub-segments of the outer intervening member.

In the present invention, the annular members arranged between the sub-segments of the outer intervening member may preferably be O-rings made of an elastic material, such as rubber, synthetic rubber, or a synthetic resin. The annular members, when made of an elastic material, follow the flexing of the casing to deform and securely hold the inner intervening member.

In the medical handpiece of the present invention, the outer intervening member is arranged around the inner intervening member, and more specifically, a plurality of sub-segments of the outer intervening member are arranged around each segment of the inner intervening member. The annular members, preferably made of an elastic material, are arranged between the sub-segments of the outer intervening member. Thus even when the casing of the medical handpiece is flexed for a relatively large angle from its axis, the inner intervening member is inhibited from displacing, since the inner intervening member is restrained by the annular members, and hardly affected by the force from the outer intervening member. This reduces the load on the shank applied by the contact with the inner intervening member, and shaking generated during rotational driving of the cutting tool may be inhibited.

PREFERRED EMBODIMENTS OF THE INVENTION

Figure 1:
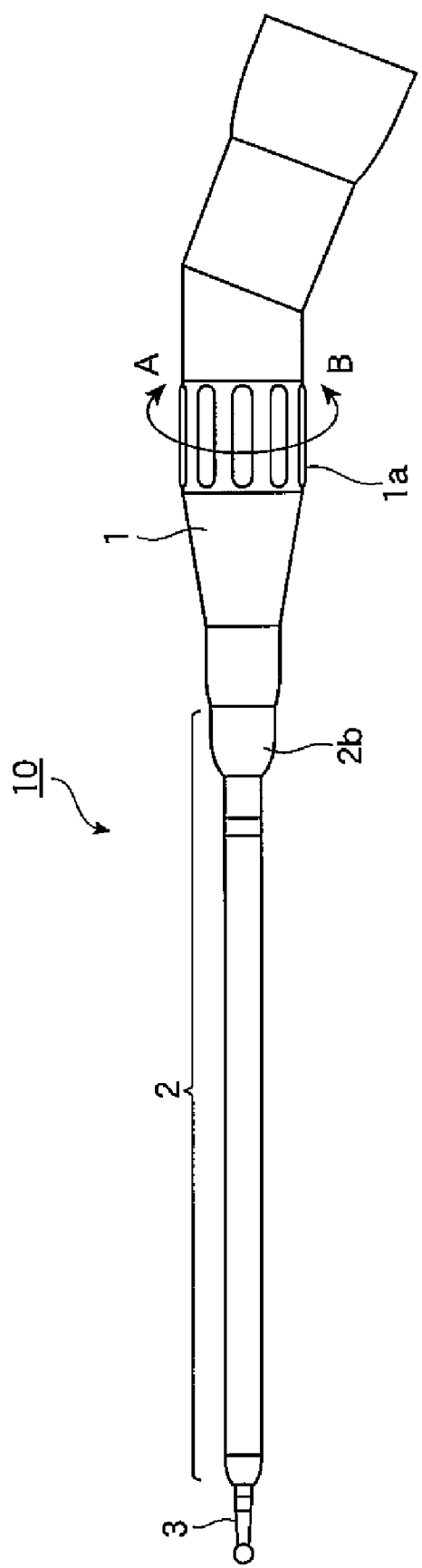
FIG. 1 is a side view of an embodiment of the present invention.

The present invention will now be explained with reference to the attached drawings.

The medical handpiece 10 according to an embodiment of the present invention has handpiece body 1, casing 2 connected to the body 1, and cutting tool 3 inserted and placed in the casing 2. The proximal end of the cutting tool 3 is detachably held in the handpiece body 1, and driven by a drive source (not shown). The medical handpiece 10 is formed such that the medical practitioner may flex the casing 2 and the cutting tool 3 over the range of about 30 degrees or less simply by holding the casing 2 with fingers and applying force. When flexed, the casing 2 undergoes plastic deformation, and shank 3a of the cutting tool 3 inside the casing 2 undergoes elastic deformation.

Figure 2:
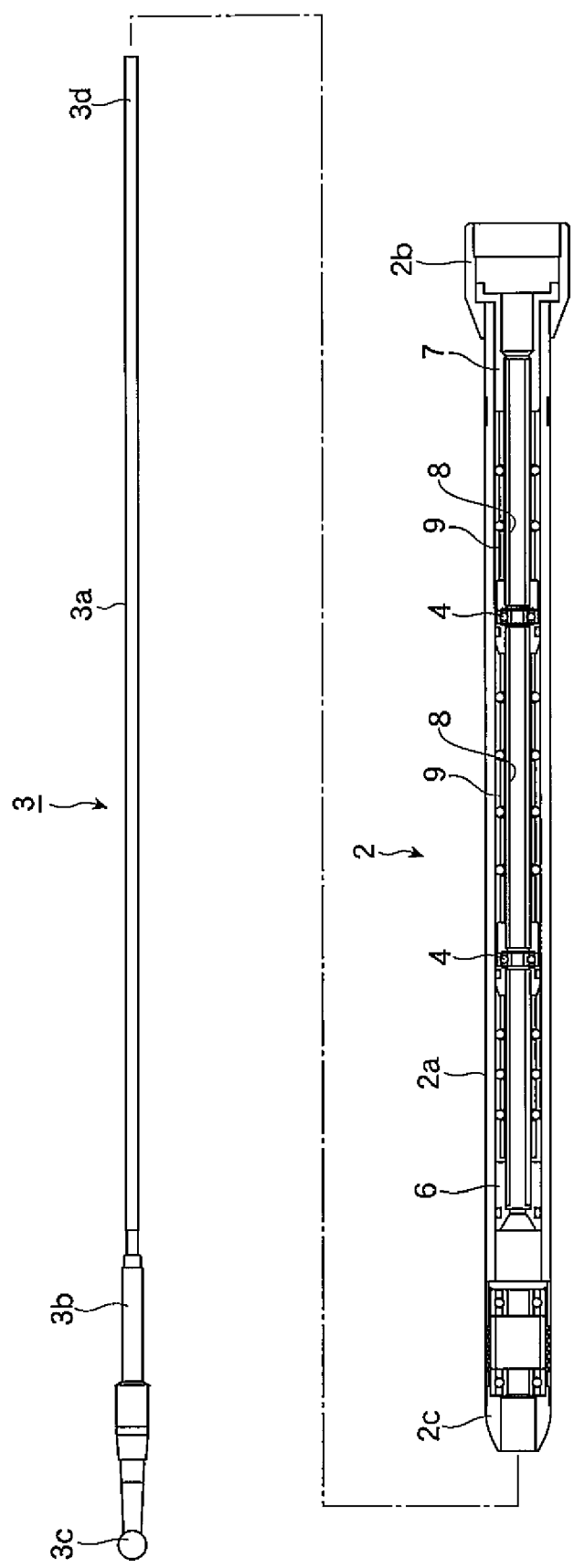
FIG. 2 is a sectional and side views of the casing and the cutting tool, respectively, of a medical handpiece according to the present invention.

As shown in FIG. 2, the cutting tool 3 has shank 3a and cutting bur 3c provided at the distal end of the shank 3a via bearing support 3b, for cutting the treatment site. The shank 3a is deformable with respect to the axial direction over the range of about 30 degrees or less within the elastic limit, and is made of a metal material such as stainless steel.

Figure 3:
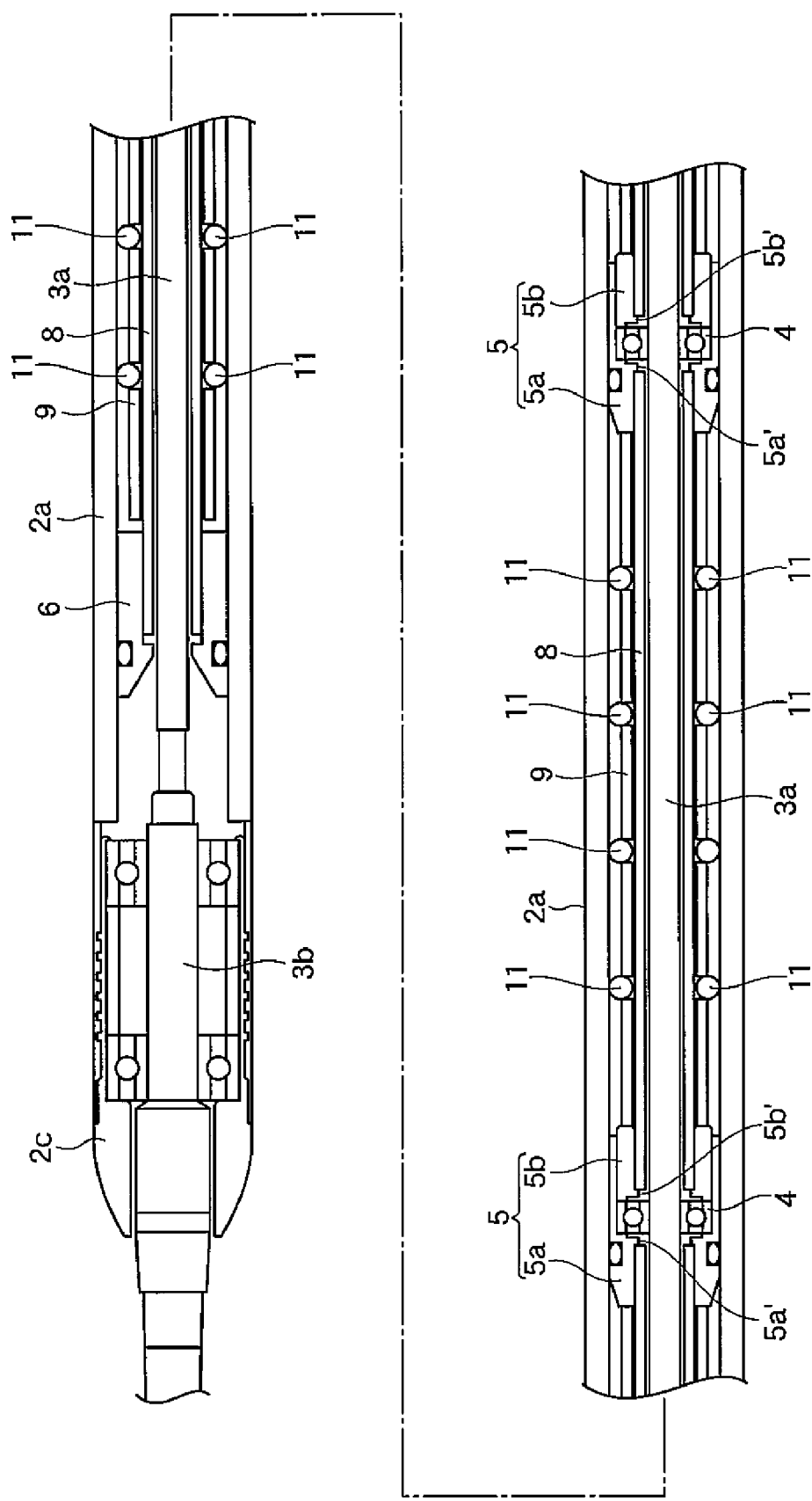
FIG. 3 is an enlarged sectional view of part of the casing and the cutting tool of the medical handpiece of FIG. 1.

Referring to FIGS. 2 and 3, the casing 2 includes metal pipe 2a, connecting member 2b, and casing cap 2c.

The metal pipe 2a is made of, for example, a stainless steel or titanium material, and has a relatively thin wall thickness, such as about 0.1 to about 0.8 mm, so that it plastically deforms without fracture when flexed for about 30 degrees or less from the axial direction.

Inside the metal pipe 2a, bearing members 4 are arranged at a plurality of locations. Each bearing member 4 is pre-assembled with fixing members 5a and 5b, inserted into the metal pipe 2a, and fixed at a predetermined position in the metal pipe 2a by pressure-fitting the fixing member 5a in the metal pipe 2a. The fixing members 5a and 5b have flanges 5a' and 5b', respectively, projecting inwards from the inner surface.

Further inside the metal pipe 2a, stop 6 for intervening member is pressure-fitted near the distal end, while stop 7 for intervening member is screwed on to the proximal end. The stops 6 and 7 for intervening member define the limits of displacement of first and second intervening members 8 and 9 (to be discussed later) in the thrust (axial) direction, at the distal and proximal ends, respectively, of the metal pipe 2a. When the casing 2 is flexed into a certain shape, the shank 3a may contact the stop 6, where the stop 6 functions as a sliding bearing.

Figure 4:
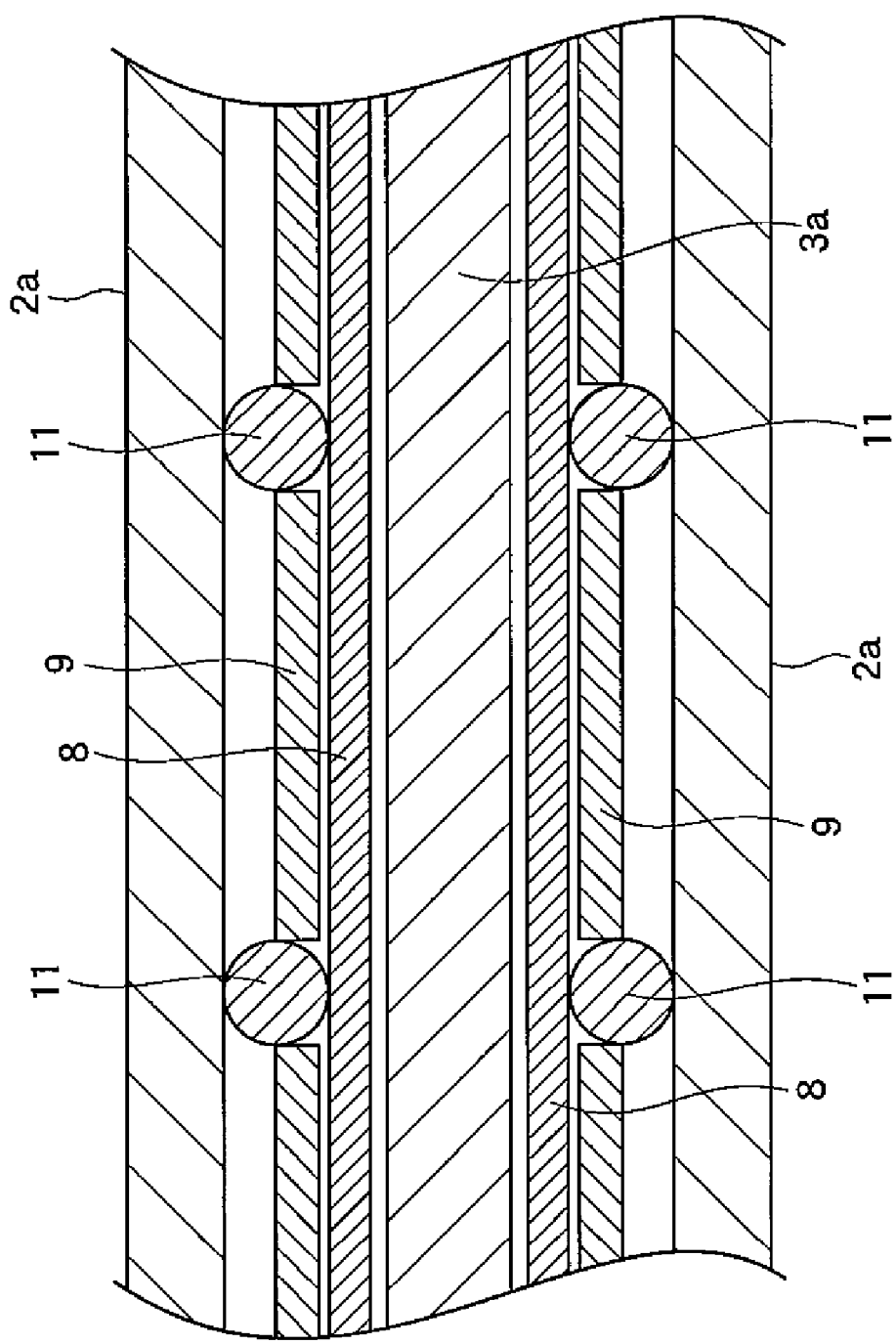
FIG. 4 is an enlarged sectional view of part of FIG. 3.

FIG. 4 is an enlarged sectional view of part of FIG. 3. Referring to FIGS. 2 to 4, first tubular intervening member 8 is composed of a plurality of segments, for example, three segments in this embodiment. Each segment of the first intervening member 8 is arranged between or on the distal or proximal side of the bearing members 4, and the ends of the segments abut the flanges 5a' or 5b' of the fixing members 5a or 5b so that the displacement of the first tubular intervening member 8 in the thrust direction is prevented. Around the first intervening member 8 are provided second tubular intervening member 9, which is composed of a plurality of segments, for example, three segments in this embodiment. Each segment of the second intervening member 9 is arranged between or on the distal or proximal side of the bearing members 4, and is further divided into a plurality of sub-segments. O-rings 11 are fit on the outer surface of the first intervening member 8 between the sub-segments of the second intervening member 9. Each O-ring 11 is made of an elastic material and has an outer diameter that is larger than that of the second intervening member 9. The O-ring 11 preferably has an outer diameter that is substantially the same as the inner diameter of the casing 2, so that the O-rings 11 are fit on the inner surface of the casing.

The first intervening member 8 has elasticity that allows it to follow the deformation of the casing 2, and is sized to be slightly displaceable in the thrust direction but not displaceable in the radial direction. The first intervening member 8 receives the shank 3a of the cutting tool 3 therein. When the casing 2 is flexed, the shank 3a is very likely to be brought into contact with the first intervening member 8, where the first intervening member 8 functions as a sliding bearing for the shank 3a. In this regard, the first intervening member 8 is made of a material having both heat resistance and abrasion resistance, e.g. a synthetic resin such as a fluororesin.

O-rings 11 are arranged between the sub-segments of the second intervening member 9, and the distal and proximal segments of the second intervening member 9 contact the fixing member 5a or 5b to prevent shaking caused by the bearing members 4. The second intervening member 9 is made of an elastic material that allows it to follow the deformation of the casing 2, and is sized to be slightly displaceable in both the radial and thrust directions.

The handpiece body 1 is provided with an operation ring 1a on its grip. On one end of the body 1 distal to the operation ring 1a, the connecting member 2b of the casing 2 is screwed, whereas the other end of the body 1 proximal to the operation ring 1a is configured to be connected to a drive section, such as a motor (not shown). The handpiece body 1 is provided inside with a conventional chuck mechanism (not shown) for detachably holding, by rotational operation of the operation ring 1a, the proximal end of the shank 3d of the cutting tool 3 inserted through the casing 2. For example, when the operation ring 1a is rotated in the direction of arrow A in FIG. 1, the proximal end 3d of the shank 3a is released from the fixed holding by the chuck mechanism to allow the cutting tool 3 to be detached. When the operation ring 1a is rotated in the direction of arrow B in FIG. 1, the proximal end 3d of the shank 3a is fixedly held by the chuck mechanism to prevent the cutting tool 3 to be detached.

Next, the function of the medical handpiece 10 having the above structure will be explained.

In the medical handpiece 10, when the casing 2 is flexed, the shank 3a of the cutting tool 3 and the first and second intervening members 8 and 9 are elastically deformed correspondingly. In this curved state, when the cutting tool 3 is rotatably driven, the shank 3a is rotated on the support of the bearing members 4 to be rotationally driven smoothly.

Even when the casing 2 is flexed relatively greatly from its axial direction, radial displacement of the first intervening member 8 is inhibited under the restraint by O-rings 11. In addition, the outer diameter of the O-rings 11 that is larger than that of the second intervening member 9 hardly allows the force from the second intervening member 9 to affect on the first intervening member 8. Thus load applied on the shank 3a of the cutting tool 3 by the contact with the first intervening member 8 is decreased, and shaking during rotation of the cutting tool 3 may be inhibited.

When the casing 2 takes a certain curved shape, the shank 3a may be pressed relatively hard against the bearing members 4. In such a state, the bearing members 4 are anticipated to generate disadvantageously increased shaking. However, in the medical handpiece 10 according to the present invention, the first and second intervening members 8 and 9, which are of elastic nature, softly contact the fixing members 5a and 5b arranged on the proximal and distal sides of each bearing member 4, so that the shaking of the bearing members 4 may be inhibited at a relatively low level.

While the present invention has been explained taking a drill for transnasal bone surgery as an example, the present invention may equally be applied to medical handpieces wherein a cutting tool with a shank is detachably inserted and held in a relatively elongate casing.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A medical handpiece comprising:
a cutting tool having a flexible shank and a cutting bur provided at a distal end of said shank for cutting a treatment site,
a tubular casing for receiving the cutting tool therein,
wherein said casing and said cutting tool are flexible for a predetermined angular range, where the casing undergoes plastic deformation and the shank of the cutting tool undergoes elastic deformation,
a handpiece body detachably holding a proximal end of the cutting tool and transmitting power from a drive source to the cutting tool,
a plurality of bearing members disposed in the casing rotatably supporting the shank of the cutting tool,
an inner flexible tubular intervening member for receiving the shank of the cutting tool therein, wherein said inner intervening member is composed of a plurality of continuous segments, each segment being arranged between or on distal or proximal side of said bearing members, and
an outer flexible tubular intervening member arranged around said inner intervening member, wherein said outer intervening member is composed of a plurality of segments, each segment being arranged between or on distal or proximal side of said bearing members correspondingly to each continuous segment of said inner intervening member,
wherein each segment of said outer intervening member is further composed of a plurality of continuous sub-segments, said plurality of continuous sub-segments of said outer intervening member being arranged around each continuous segment of said inner intervening member, and a plurality of annular members having the outer diameter that is larger than the outer diameter of said outer intervening member are arranged between said sub-segments of the outer intervening member.

2. The medical handpiece according to claim 1, wherein said annular members are fit on the outer surface of the inner intervening member.

3. The medical handpiece according to claim 1, wherein said annular members are fit on the inner surface of the casing.

4. The medical handpiece according to claim 1, wherein said annular members are made of an elastic material.

5. The medical handpiece according to claim 4, wherein said annular members are O-rings.

* * * * *